United States Patent
Wolters et al.

(10) Patent No.: US 9,428,287 B2
(45) Date of Patent: Aug. 30, 2016

(54) METHODS OF FABRICATING TEST SAMPLE CONTAINERS BY APPLYING BARRIER COATINGS AFTER SEALED CONTAINER STERILIZATION

(71) Applicant: bioMérieux Inc., Durham, NC (US)

(72) Inventors: Weihua Sonya Wolters, Raleigh, NC (US); Stanley Michael Philipak, Augusta, MO (US)

(73) Assignee: bioMérieux, Inc., Durham, NC (US)

( * ) Notice: Subject to any disclaimer, the term of this patent is extended or adjusted under 35 U.S.C. 154(b) by 131 days.

(21) Appl. No.: 13/790,177

(22) Filed: Mar. 8, 2013

(65) Prior Publication Data

US 2014/0120605 A1 May 1, 2014

Related U.S. Application Data

(60) Provisional application No. 61/720,512, filed on Oct. 31, 2012.

(51) Int. Cl.
*B65B 1/04* (2006.01)
*B01L 3/00* (2006.01)
(Continued)

(52) U.S. Cl.
CPC ............... *B65B 1/04* (2013.01); *B01L 3/5082* (2013.01); *B01L 3/50825* (2013.01);
(Continued)

(58) Field of Classification Search
CPC ............... B01L 2200/0689; B01L 2200/141; B01L 2300/0854; B01L 2300/16; B01L 3/5082; B01L 3/50825; B65B 1/04; C12M 23/08; C12M 23/20; C12M 41/26; C12M 41/34

See application file for complete search history.

(56) References Cited

U.S. PATENT DOCUMENTS

| 4,528,235 A | 7/1985 | Sacks et al. |
| 4,536,425 A | 8/1985 | Hekal |

(Continued)

FOREIGN PATENT DOCUMENTS

| EP | 0460796 | 12/1991 |
| FR | 2381103 | 9/1978 |

(Continued)

OTHER PUBLICATIONS

Blow molding, Packaging technology, http://packaging-technology.org/35-blow-molding.html, Jan. 31, 2012, 26 pages, printed from the internet Sep. 6, 2012.

(Continued)

*Primary Examiner* — Nathan Bowers
*Assistant Examiner* — Lydia Edwards
(74) *Attorney, Agent, or Firm* — Myers Bigel & Sibley, P.A.

(57) ABSTRACT

Methods of fabricating a culture container include molding a single monolithic layer of polymeric material into a container body having a container shape; introducing a colorimetric sensor material and growth media into the container body; introducing a gas mixture into the container body to define a headspace gas in an upper portion of the container body; attaching a stopper to the neck of the container body with the sensor material; sealing the container body with the stopper closed to define a sealed container with the growth media and the headspace gas enclosed therein; then sterilizing the sealed container; then applying a gas barrier coating to an exterior of the sterilized container body so that the sealed container has an oxygen transmission rate (cubic centimeter/container/day/atm) that is between about 0.001 to about 0.01 to thereby define a culture container that is ready-to-use and shelf stable without autoclaving.

20 Claims, 3 Drawing Sheets

(51) Int. Cl.
*C12M 1/24* (2006.01)
*C12M 1/00* (2006.01)
*C12M 1/34* (2006.01)
*G01N 33/50* (2006.01)

(52) U.S. Cl.
CPC ............ *C12M 23/08* (2013.01); *C12M 23/20* (2013.01); *C12M 41/26* (2013.01); *C12M 41/34* (2013.01); *G01N 33/5005* (2013.01); *B01L 2200/0689* (2013.01); *B01L 2200/141* (2013.01); *B01L 2300/0854* (2013.01); *B01L 2300/16* (2013.01)

(56) References Cited

U.S. PATENT DOCUMENTS

| | | |
|---|---|---|
| 4,584,823 A | 4/1986 | Nagel |
| 4,735,832 A | 4/1988 | Ichikawa et al. |
| 4,827,944 A | 5/1989 | Nugent |
| 4,911,218 A | 3/1990 | Patitsas |
| 4,945,060 A | 7/1990 | Turner et al. |
| 4,960,639 A | 10/1990 | Oda et al. |
| 4,983,432 A | 1/1991 | Bissot |
| 4,995,519 A | 2/1991 | Rose et al. |
| 5,000,804 A | 3/1991 | Nugent |
| 5,049,609 A | 9/1991 | Patitsas |
| 5,090,581 A | 2/1992 | Rose et al. |
| 5,091,467 A | 2/1992 | Beers |
| 5,094,955 A * | 3/1992 | Calandra et al. ......... 435/288.7 |
| 5,162,229 A | 11/1992 | Thorpe et al. |
| 5,164,796 A | 11/1992 | Di Guiseppi et al. |
| 5,217,876 A | 6/1993 | Turner et al. |
| 5,356,052 A | 10/1994 | Poynter |
| 5,472,753 A | 12/1995 | Farha |
| 5,718,967 A | 2/1998 | Hu et al. |
| 5,770,394 A | 6/1998 | Berndt |
| 5,795,773 A | 8/1998 | Read et al. |
| 5,856,175 A | 1/1999 | Thorpe et al. |
| 5,860,329 A | 1/1999 | Day |
| 5,908,676 A | 6/1999 | Otaki et al. |
| 5,968,620 A * | 10/1999 | Harvey et al. ............... 428/35.9 |
| 6,123,211 A | 9/2000 | Rashid et al. |
| 6,383,166 B1 | 5/2002 | Farris |
| 6,709,857 B2 | 3/2004 | Bachur, Jr. |
| 6,860,405 B1 | 3/2005 | Poynter |
| 7,028,862 B2 | 4/2006 | Poynter |
| 7,078,453 B1 | 7/2006 | Feeney et al. |
| 7,119,138 B1 | 10/2006 | Feeney et al. |
| 7,211,430 B2 | 5/2007 | Schwarz et |
| 7,473,729 B2 | 1/2009 | Feeney et al. |
| 7,803,305 B2 | 9/2010 | Ahern et al. |
| 7,985,188 B2 | 7/2011 | Felts et al. |
| 8,144,199 B2 | 3/2012 | Takenaka et al. |
| 2003/0175465 A1 | 9/2003 | Watanabe et al. |
| 2003/0215652 A1* | 11/2003 | O'Connor ................. C08J 7/04 428/451 |
| 2004/0101955 A1 | 5/2004 | Whitley |
| 2006/0037287 A1 | 2/2006 | De Vos |
| 2006/0110615 A1 | 5/2006 | Karim et al. |
| 2007/0213446 A1 | 9/2007 | Feeney et al. |
| 2008/0014429 A1 | 1/2008 | Su et al. |
| 2008/0131707 A1 | 6/2008 | Feeney et al. |
| 2009/0162587 A1 | 6/2009 | Wilkinson et al. |
| 2009/0285722 A1 | 11/2009 | Soskey et al. |
| 2010/0068755 A1 | 3/2010 | Walsh et al. |
| 2011/0081714 A1 | 4/2011 | Wilson et al. |
| 2011/0081715 A1* | 4/2011 | Robinson et al. ......... 435/304.1 |
| 2011/0124028 A1 | 5/2011 | Robinson et al. |
| 2011/0186537 A1 | 8/2011 | Rodriguez San Juan et al. |
| 2011/0252899 A1 | 10/2011 | Felts et al. |
| 2012/0123345 A1 | 5/2012 | Felts et al. |

FOREIGN PATENT DOCUMENTS

| | | |
|---|---|---|
| WO | WO93/04118 | 3/1993 |
| WO | WO94/26874 | 11/1994 |
| WO | WO2011/014429 | 2/2011 |
| WO | WO2011/016838 | 2/2011 |
| WO | WO2011/041471 | 4/2011 |

OTHER PUBLICATIONS

Guidance for Industry, Sterile Drug Products Produced by Aseptic Processing—Current Good Manufacturing Practice, Pharmaceutical CGMPs, U.S. Department of Health and Human Services, Food and Drug Administration, Center for Drug Evaluation and Research (CDER), Center for Biologics Evaluation and Research (CBER), Office of Regulatory Affairs (ORA), Sep. 2004, 19 pages.

Gruniger et al., Influence of defects in $SIO_x$ thin films on their barrier properties, Thin Solid Films, 2004, pp. 308-312, vol. 459.

International Search Report and Written Opinion for corresponding PCT Application No. PCT/US2013/066051, date of mailing Mar. 13, 2014, 9 pages.

* cited by examiner

FIG. 4

METHODS OF FABRICATING TEST SAMPLE CONTAINERS BY APPLYING BARRIER COATINGS AFTER SEALED CONTAINER STERILIZATION

RELATED APPLICATIONS

This application claims the benefit of and priority to U.S. Provisional Application Ser. No. 61/720,512, filed Oct. 31, 2012, the contents of which are hereby incorporated by reference as if recited in full herein.

FIELD OF THE INVENTION

This invention relates to methods for fabricating containers that are particularly suitable for culturing biosamples.

BACKGROUND OF THE INVENTION

Bottles for collection or culturing of blood and other biological samples are known in the art. See, e.g., U.S. Pat. Nos. 4,945,060; 5,094,955; 5,860,329; 4,827,944; 5,000,804; 7,211,430 and U.S. patent application publication 2005/0037165.

Sample culture bottles or containers typically contain a headspace gas composition to facilitate the recovery of organisms. The blood culture container is made of a suitable gas-impermeable material to ensure that the integrity of the gas composition in the headspace of the bottle is maintained throughout the shelf life of the bottle. For typical analysis, the container should ideally remain visually optically transmissive, typically transparent, through its life to allow for one or more of (i) manual or electronic observation of the contents of the container, (ii) measuring fill level when using the container, (iii) visual observation of contents after culturing or growth, and (iv) a reading of an internal sensor in the container that detects microbial growth.

Several types of blood culture bottles have been used that limit gas diffusion into or out of the bottle. One type is a glass vial with an elastomeric seal. The glass vial itself provides the gas barrier. However, if a glass vial is dropped it may break, exposing the user to glass shards and, potentially, biologically hazardous materials. Furthermore, the nature of glass manufacturing can leave undetectable microcracks in the glass, which under the pressure of microbial growth in the vial can lead to bottle rupturing, and, again, exposure to biohazardous materials.

A second type of blood culture bottle is a multi-layer plastic vial. See, e.g., U.S. Pat. No. 6,123,211 and U.S. Patent Publication 2005/0037165. The multi-layer plastic vial is fabricated from two plastic materials that each serve different functions. For example, the interior and exterior layers of the vials can be produced from polycarbonate, which offers the strength and rigidity required for product use. Likewise, polycarbonate can withstand higher temperatures required for autoclave of the product during manufacture and remains transparent. However, the polycarbonate does not provide a sufficient gas barrier. The middle material layer can be fabricated from nylon, which provides the required gas barrier. The nylon, by itself, does not have the necessary rigidity and strength to withstand the autoclave temperatures required during the manufacture of blood culture bottles, since it would not remain transparent if exposed to moisture or autoclaved. The multilayer plastic vial offers advantages over the glass vials. However, multi-layer plastic vials are produced with relatively complex manufacturing methods and the vials are consequently relatively expensive.

More recently, single layer plastic bottles have been proposed which employs an autoclave or bottle sterilization process to provide the necessary cleanliness/sterility. See, e.g., U.S. Patent Publication No. 2011/0081714, the contents of which are incorporated by reference as if recited in full herein.

Despite the above, there remains a need for cost-effective test sample containers and fabrication methods.

SUMMARY OF EMBODIMENTS OF THE INVENTION

Embodiments of the invention are directed to methods for sterilizing test sample containers prior to applying an external gas barrier coating.

Some embodiments are directed to methods of fabricating/producing a culture container. The methods include: (a) introducing a colorimetric sensor material into a molded container body of a single monolithic layer of polymeric material, the container body having a container shape with a bottom and an upwardly extending wall that merges into an upper portion having a shoulder and neck the container body; (b) introducing growth media into the container body; (c) introducing a gas or gas mixture into the container body under vacuum to define a headspace gas in an upper portion of the container body; (d) attaching a stopper to the neck of the container body with the sensor material; (e) sealing the container body with the stopper with the growth media and the headspace gas enclosed therein; then (f) sterilizing the sealed container; then (g) applying a gas barrier coating to an exterior of the sterilized container body so that the sealed container has an oxygen transmission rate (cubic centimeter/day/atm air/container) that is between about 0.00001 to about 0.1 to thereby define a culture container that is ready-to-use and shelf stable without post-coating autoclaving.

The step of applying the gas barrier coating can be carried out to cover all external surfaces of the container body. The step of applying can be carried out to cover a large portion (e.g., >60% of the surface area) of external surfaces of the container body.

The gas barrier coating can be in the form of a liquid, gas or liquid and gas. The gas barrier coating can be a single coating applied in a single step or a single coating applied in multiple layers. The gas barrier coating can comprise multiple coatings applied in a single step or multiple coatings applied in multiple steps/layers.

The step of applying the gas barrier coating can be carried out by one or more of: (i) spraying the sealed container body with a liquid coating solution; (ii) immersing the sealed container body in a liquid coating solution; (iii) flow or curtain coating, (iv) fluidized bed coating; and/or (v) depositing a vapor onto the container surface using photolysis method. Other coating methods may be used as is known to those of skill in the art.

The applying step can include curing the coating solution on the container body to form a thin transparent coating film that adheres to the outer surface of the container body.

The coating step can be repeated after the curing to apply a second barrier coating layer.

The coating solution could be aqueous, or organic solvent based, or solvent less.

The coating could be in the form of a liquid or gas. It could be one part coating or two part system.

The curing can be based on heat, UV, IR, radiation or forced air or gas, or reagent reaction, or combinations of same. The attached coating film could be materials chemically unchanged from the coating solution, or materials created in-situ during the coating application process by mixing two parts together, or materials created during curing process, or materials deposited via vapor.

The transparent film formed on the container surface could contain organic natured products such as polyurethane (PU), epoxies (EPDXY), polyvinylidene dichloride (PVDC), polyvinyl alcohol (PVOH), polyamide (PA), polyacrylonitrile (PAN), polyester, polyglytic acid (PGA), polylactic acid (PLA), Phenoxy, or organic salts, nanocomposites, or metal oxide such as aluminum oxide, or silica. The transparent film formed on the container surface could be modification of above materials or copolymers.

The polymeric material can include polycarbonate (PC) or cyclic olefin copolymer (COC) and/or other polyolefins such as polypropylene (PP) or polyethylene (PE), or polyester such as polyethylene terephthalate (PET) or polyethylene naphthlate (PEN), or polyamide (nylon).

The method can include, before the applying step and after the sterilization step, treating the sterile container body with plasma, flame or alcohol wipe.

The method can include, before the applying step and after the sterilization step, treating the sterile container body with a primer or other adherent promoting material.

The method can include, after applying the gas barrier coating, applying a top coat.

The method can include, after applying the gas barrier coating, applying a top coat to provide at least one of the following characteristics: (i) inhibit or prevent the gas barrier coating from having direct contact with moisture in the air; (ii) help the mechanical property such as abrasion resistance of the gas barrier coating, or (ii) to further improve the gas barrier property.

The applied gas coating is a transparent film that has a thickness that is between about 1-1000 microns, or vapor deposited layer having a thickness between 10-1000 microns.

In some particular embodiments, the step of applying the gas coating can be carried out using an aqueous solution that comprises a polyetheramine. Other coatings may be used.

In particular embodiments, the step of applying the gas coating can be carried out using a polyepoxy-based resin and/or a polyamine based resin. Other coatings may be used.

The process can further include applying an internal coating onto interior surfaces of the container body before the introducing steps.

The container body bottom can be substantially flat.

The colorimetric sensor material can include Liquid Emulsion Silicone (LES).

The stopper can include an external attachment feature. The method can further include suspending the sealed container using the attachment feature during the applying step to thereby expose the container body to allow the coating material to coat the entire container body.

The culture container can be a blood sample container for culturing microbes in a blood sample.

The step of applying the gas barrier coating can be carried out to define a sealed container with a monolayer gas barrier coating that has an oxygen transmission rate that is between about 0.00001 and 0.1 (cubic centimeter/container/day/atm air).

The step of applying the gas barrier coating can be carried out to define a sealed container with a bi-layer gas barrier coating that has an oxygen transmission rate that is between about 0.001 to about 0.01 (cubic centimeter/container/day/atm air).

Some embodiments are directed to (an evacuated) blood culture sample containers that include: (a) an elongate molded monolithic single layer polymeric container body having an upwardly extending, visually transmissive wall with a wall thickness that is between about 0.5 to 5 mm; (b) a colorimetric sensor in the container body; (c) organism growth media in the container body; (d) an elastomeric stopper sealably attached to the container; and (e) a thin visually transmissive gas barrier coating on the sealed container body. The gas barrier coating is non-sterile at shipment and during a defined shelf life the sealed container with the gas barrier coating has an oxygen transmission rate that is between about 0.001 and 0.01 (cc/container/day/atm air), on average.

The single layer polymeric wall thickness can, in some particular embodiments, be about 1.5 mm (nominal). The gas barrier coating can depend on the material(s) used, and can be, for example, between about 2 microns to about 1000 nanometers, such as between about 2-10 microns, between about 10-50 microns, or between about 50-100 microns, or, for additional examples, between about 10-50 nanometers, between about 50-200 nanometers, between about 200-500 nanometers, and between 500-1000 nanometers.

The sealed container can also include a metallic cap extending over the stopper and crimped to attach to an upper portion of the container neck.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

The present invention now is described more My hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

The term "sample" refers to a target material undergoing testing or analysis for content. The sample can be a food sample, an environmental sample (water, air, soil, etc.) or a biosample. The testing can be for quality control of food produced in a commercial manufacturing facility, for the EPA (Environmental Protection Agency of the U.S. Government), for environmental toxins or hazardous materials that are man-made, intentional or not, or medical (clinical diagnostic) purposes.

The term "biosample" refers to human or animal tissue, blood, blood plasma or serum, blood fractions, joint fluid, urine, semen, saliva, feces, cerebrospinal fluid, gastric contents, vaginal secretions, tissue homogenates, bone marrow aspirates, bone homogenates, sputum or lavages, aspirates, swabs and swab rinsates, blood products (e.g., platelets, serum, plasma, white blood cell fractions, etc.), donor organ or tissue samples, and the like. In one embodiment, the biological sample tested is a blood sample, urine, cerebral spinal fluid, lavages, mucus or other solid or liquid samples for analysis which may have microbes, microorganisms, toxins and/or cellular material or other constituents of interest. Embodiments of the invention may be suitable for veterinarian use, medical human use or research for human and/or with laboratory animals. In general, any known test sample (e.g., a biological sample or specimen) can be used. For example, the test sample can be a clinical or non-clinical sample suspected of containing one or more microbial agents. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and biowarfare samples.

The term "sterile" and derivatives thereof mean that the noted device or material meets or exceeds defined (e.g., food or medical) guidelines of sterility so as to be substantially (if not totally) free of contaminants for at least a defined shelf life so as to be suitable for intended uses, e.g., clinical, health, or consumer product testing for the presence of toxins, microbes, microorganisms or other target constituents in a sample undergoing analysis. The sample can undergo analysis while held in the container. The sample may be transferred after transport and/or culturing in the container for analysis.

The term "aseptic" is used interchangeably with the word "sterile". In some embodiments, the aseptic processing or fabrication complies with GMP (Good Manufacturing Practice) industry guidelines such as those associated with Guidance for Industry—Sterile Drug Products Produced by Aseptic Processing—Current Good Manufacturing Practice, U.S. Department of Health and Human Services Food and Drug Administration, September 2004.

The term "parison" refers to a preform of material that is subsequently blown into a shape defined by an enclosed mold using pressurized gas using conventional blow molding processes (typically extrusion-based methods) as is well known to those of skill in the art.

The term "automatic" means that the operation can be carried out using automated electromechanical equipment, rather than with manual labor.

The term "substantially impermeable" means that the sealed container has low permeability, e.g., an oxygen transmission rate ("OTR") (cubic centimeter/container/day/atm air) that is between about 0.00001 to about 0.1 cc/day/atm. As described below, sealed containers contemplated by embodiments of the invention are substantially impermeable. The sealed containers 10 typically have oxygen transmission rates (cubic centimeter/container/day/atm air) that is between 0.001 to about 0.01. The test conditions can be at 1 atm, a relative humidity, RH %, that is 40% and a room temperature that is 20 degrees C. The term "day" means 24 hours. The oxygen transmission rate can be determined using ASTM D-3985-02 or other suitable protocols.

The reference to "atm" means "atm air" unless stated otherwse. OTR can be expressed with just "atm" which assumes air or "atm air." In actual MOCON testing, the test gas is 100% oxygen. The data from this test protocol can be converted into test gas of 21% oxygen, which is air's composition, to represent actual "use" environments. In testing, 100% oxygen test gas can be used to accelerate the testing time as is well known to those of skill in the art. As is known to those of skill in the art OTR testing can be carried out using a MOCON Oxtran 2/61 Oxygen Permeability Instrument per standard ASTM F-1307

The term "thin" with reference to the external or outer oxygen/gas barrier coating refers to a thickness of between about 1 micron to about 1000 nanometers, such as between about 1-1000 microns, typically between about 5-500 microns, more typically between about 5-100 microns, such as about 10 microns, 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, and about 100 microns, or between 10-1000 nanometers.

The term "draw volume" refers to draw of deionized water as is known to those of skill in the art.

Figure 1:
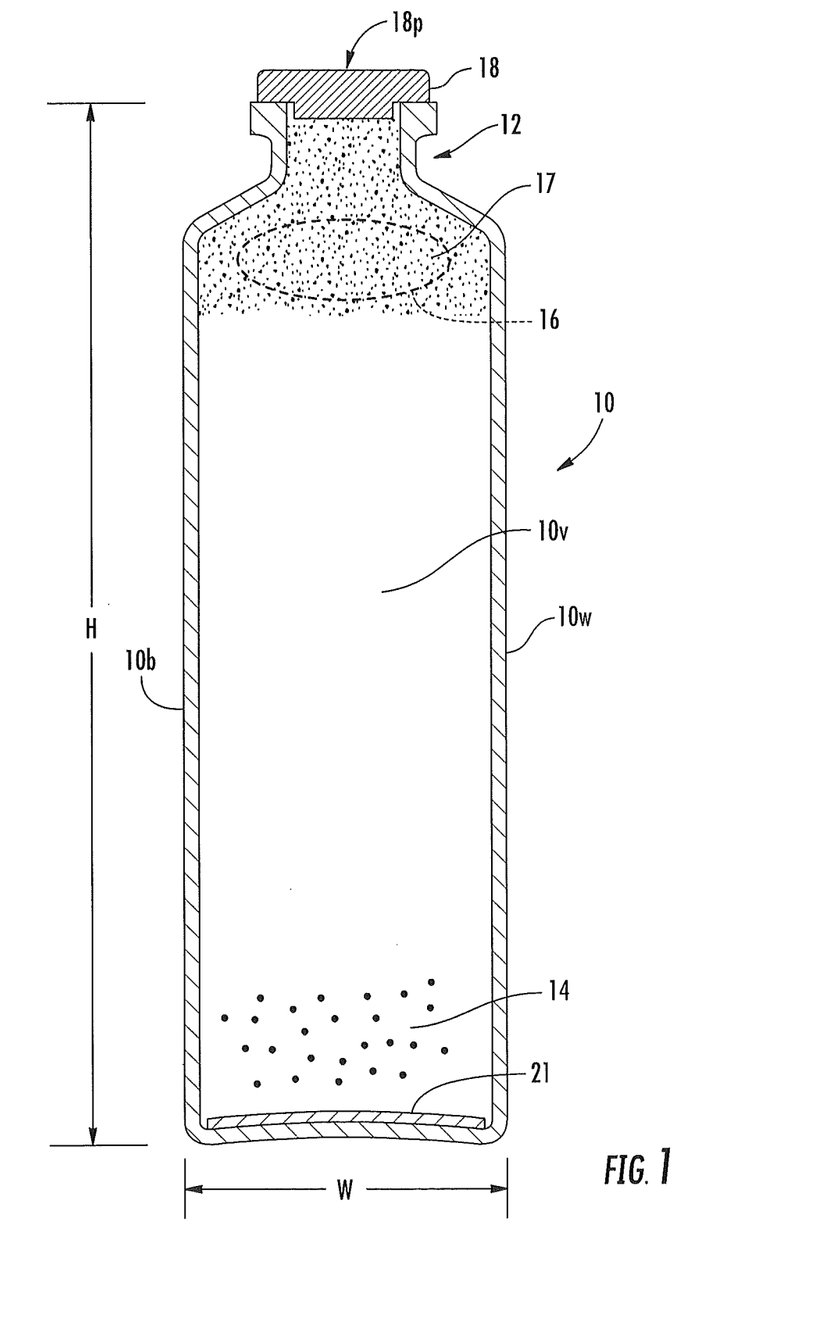
FIG. 1 is a sectional view of an exemplary culture container according to embodiments of the present invention.
Figure 2:
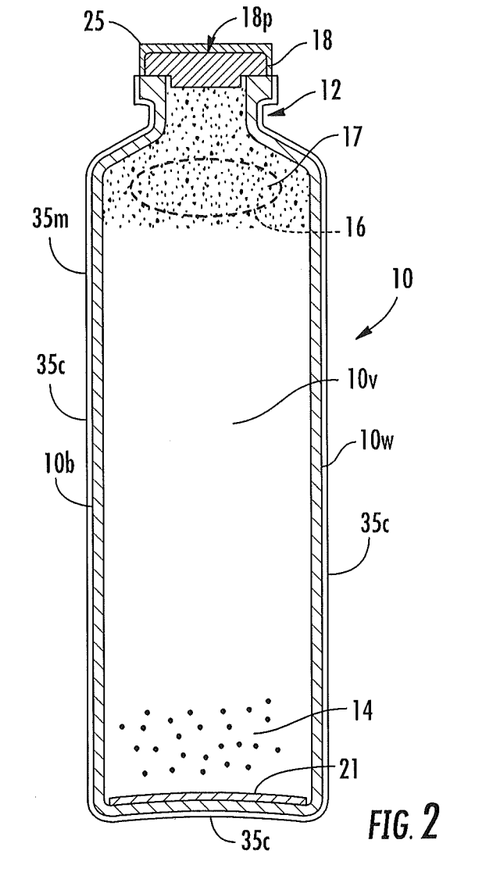
FIG. 2 is a sectional view of an exemplary culture container with an external barrier coating according to embodiments of the present invention.

Turning now to the figures, FIGS. 1 and 2 illustrate an exemplary sample culture container 10. The containers 10 are typically elongated containers with an internal volume 10$v$ and an outer wall 10$w$ having an outermost width dimension (W) being less than a height dimension (H). In some embodiments, the height (H) is greater than twice the width (W), e.g., H>2W. In some embodiments, the containers 10 have tubular bodies with maximum outer diameters between about 1-2 inches and heights of between about 2-5 inches. In some particular embodiments, the containers 10 have an outer diameter of about 1.36 inches (34.6 mm) and a height that is about 4.68 inches (119 mm).

The container 10 can have a body shape in the form of a standard culture bottle (e.g., a blood culture bottle). However, the description of a culture bottle (e.g., a blood culture bottle) is offered by way of example and not limitation. The container 10 may include a bar code label (not shown) for automated reading of patient data and/or test parameters of the content of the container 10. In some embodiments, the top portion of the container 10 can include a narrow portion or neck 12. The container 10 may also include an elastomeric stopper 18 optionally having a self-(re)sealing pierceable material and/or septum 18$p$.

The container 10 can have a headspace 16 that can accommodate a target (non-air) gas or gas mixture. The gas 17 in the headspace 16 can be introduced into the container 10 during manufacture as will be discussed below. The gases introduced into the container could be oxygen, nitrogen, carbon dioxide, helium, or combination of these gases. The gas could be introduced into the container at a vacuum. The vacuum can be between 3-20 inch Hg, such as about 4.5 inch, about 8 inch, or about 17 inch Hg.

In some embodiments, a cap 25, such as an aluminum or other suitable material can be placed on the top of the container 10 over the stopper 18 as shown in FIG. 2. Typically, the cap 25 is crimped to attach to the upper portion of the container body.

In some embodiments, the container 10 may also have an internal sensor 21 (e.g., a Liquid Emulsion Silicone "LES" sensor) formed or placed in the bottom portion of the container 10 for purposes of optic (e.g., visual such as colorimetric or fluorescent) detection of the internal content, e.g., presence of microbial growth in the container 10. The container 10 can include a body with an optically transmissive material. The body 10$b$ can have a wall 10$w$ that is substantially transparent or sufficiently translucent at the time of testing to allow for visual detection of container content therein. A variety of sensor technologies are available in the art and may suitable. In some embodiments, the detection unit takes colorimetric measurements as described in the U.S. Pat. Nos. 4,945,060; 5,094,955; 5,162,229; 5,164,796; 5,217,876; 5,795,773; and 5,856,175, which are incorporated by reference as if recited in full herein. A positive container can be identified depending upon these colorimetric measurements, as explained in these patents. Alternatively, detection could also be accomplished using intrinsic fluorescence of the microorganism, and/or detection of changes in the optical scattering of the media (as disclosed, for example, in copending U.S. patent application Ser. No. 12/460,607, filed Jul. 22, 2009 and entitled, "Method and System for Detection and/or Characterization of a Biological Particle in a Sample"), which is also incorporated by reference as if recited in full herein. In yet another embodiment, detection can be accomplished by detecting or sensing the generation of volatile organic compounds in the media or headspace of the container.

Exemplary analytical instruments for analyzing the bottles for presence of organisms include U.S. Pat. Nos. 4,945,060; 5,094,955; 6,709,857 and 5,770,394, U.S. Patent Publication 2011/0124028 and PCT Publication WO 94/26874. The contents of these documents are hereby incorporated by reference as if recited in full herein. As described in more detail in U.S. Patent Publication 2011/0124028 incorporated by reference hereinabove, an automated detection system may contain one or more work-flow stations for obtaining one or more measurements, readings, scans and/or images of a specimen container, thereby providing information, such as, container type, container lot number, container expiration date, patient information, sample type, test type, fill level, weight measurement, and the like.

The container 10 may further comprise a growth or culture medium 14 for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 10. The growth media 14 can comprise culture growth media for enhancing or promoting microorganism growth. The media can include a growth media for an aerobic organism or an anaerobic organism.

After a sufficient time interval to allow amplification of microorganisms (this time interval varies from species to species), the container 10 can be tested within an automated detection system for evaluating the presence of microbial or microorganism growth. The testing may occur continuously or on a periodic basis so that the container content can be electronically determined as positive for microorganism growth as soon as possible.

The container 10 can include a body 10b that is molded. The body 10b can be a molded polymeric body 10b (e.g., a thermoplastic material body) made from a single layer of polymeric (plastic) monolithic material. Examples of useful materials include, but are not limited to, polycarbonate, polyolefin such as polypropylene (PP), polyethylene (PE), or cyclic copolymer (COC), polyester such as, polyethylene terephthalate (PET) or polyethylene napthalate (PEN), or polyamide (nylon) or other well-known materials in the plastics art. Amorphous plastics such as amorphous nylon exhibit high transparency and may also be suitable. The polymer material can comprise a thermoplastic material and can include for, example, one or combinations of materials including one or more of polycarbonate, polyolefin, polyester, polyethylene and nylon. The body 10b can be a molded body of a single monolithic layer of thermoplastic material that can have a wall thickness between 0.5 mm to 5 mm, such as about 0.5 mm, about 0.6 mm, about 0.7 mm, about 0.8 mm, about 0.9 mm, about 1 mm, about 1.25 mm, about 1.5 mm, about 1.75 mm, about 2 mm, about 3 mm, about 4 mm, or about 5 mm.

As shown in FIG. 2, the container body 10b may include an external barrier material 35m of one or more layer or layers such as one or more, e.g., two or three, coating layers 35c of a gas barrier material. The gas barrier coating 35c is substantially gas impermeable and is visually transmissive, typically transparent, after solidifying and/or curing to the outerwall of the container body 10b.

However, unlike prior known processes, embodiments of the present invention apply the gas barrier material 35m after the container body 10b, sealed shut with internal content such as the sensor material 21 and the growth media 14, is sterilized. The sealed container 10 can be filled, sealed and autoclaved prior to application of the barrier material 35m so that the barrier material 35m is not exposed to autoclaving temperatures or other processing environments or conditions during filling and/or sterilizing, thereby inhibiting barrier degradation or damage that can be caused by such processing. Autoclaving is the most effective and most efficient means of sterilization. As is well known, autoclaves operate on a time/temperature relationship. Higher temperatures ensure more rapid killing. Some standard autoclave temperature/pressures employed are 115° C./10 p.s.i., 121° C./15 p.s.i., and 132° C./27 p.s.i.

The container body 10b with the external barrier material 35m is visually transmissive and substantially impermeable at normal environmental pressures allowing for a suitable shelf life. In some embodiments, the container 10 with the external coating or barrier material 35m has an oxygen transmission rate (cubic centimeter/container/day/atm air) that is between 0.00001 to about 0.1, more typically between 0.001 to 0.01 (on average). In some embodiments, the container 10 with a single layer container body has an oxygen transmission rate (cc/container/day/atm air) that is reduced at least 10× for some single layer polymeric materials alone (such as cyclic olefin copolymer) to about 100× for others, such as single layer polycarbonate, after the gas barrier coating is applied and in a ready to use configuration without post-barrier coating autoclaving.

The barrier material 35m can comprise one or more external coating layers 35c. If more than one coating layers is used, the coating layers can be of the same or different materials. In some embodiments, the external coating 35c can be a thin mono-layer transparent film or layer that has a thickness that is between about 5 microns to about 100 nanometers, such as between about 5-500 microns. The external coating 35c can comprise a thin vapor-deposited layer of between about 10-100 nanometers or between about 5-500 microns. In some embodiments, the external coating 35c can be a thin bi-layer transparent film that has a thickness that is between about 5-500 microns. In some embodiments, the external coating 35c can comprise or consist only of a thin vapor-deposited layer of 10-100 nanometers. A first layer of barrier material can be applied and cured into an attached coating by exposing the container with the barrier material to a defined temperature for a defined time, typically between about 50-130 degrees Celsius for between about 10 seconds to about 60 minutes. The first (or only) layer of barrier material can alternatively or additionally be UV cured suing a UV light source or other cure mechanism or source. Additional layers of the coating can be applied and the curing can be repeated if desired.

In some embodiments, the container 10 has a molded, single layer polymeric wall thickness of about 1.5 mm (nominal). The gas barrier coating 35c can depend on the material(s) used, and can be between 1 or 2 microns to about 1000 nanometers such as, for example between about 2-10 microns, between about 10-50 microns, between about 50-100 microns or can be a thin (which may be a vapor-deposited) layer of between 10-100 nanometers.

Surface preparations can be carried out and/or adherents such as plasma, flame treatment or primers can be applied to promote coating adhesion prior to applying a respective barrier material 35m.

The container 10 can include an internal coating layer or layers such as of silica (not shown) for improved rigidity or strength and/or additional gas barrier protection.

Figure 3A:
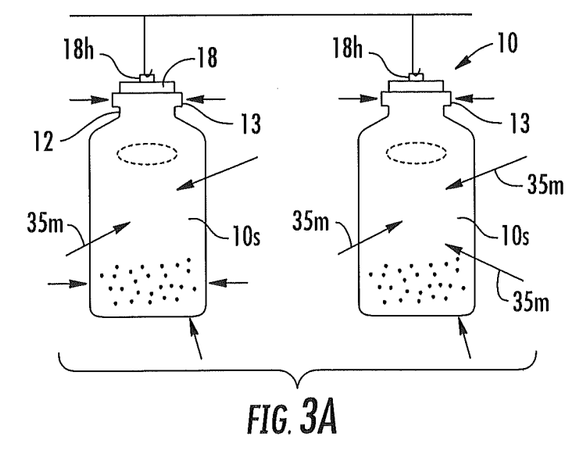
FIGS. 3A and 3B are schematic front view of pre-sterilized sealed, filled culture containers for application of an external coating material according to embodiments of the present invention.
Figure 3B:
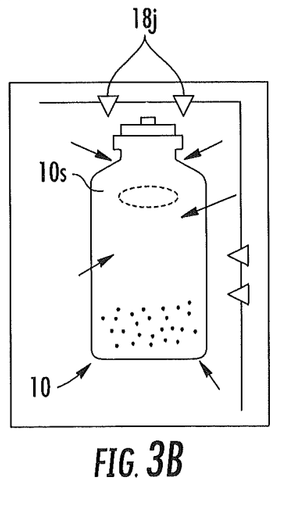

FIGS. 3A and 3B illustrate that the sterile sealed containers 10s can be exposed to the barrier material 35m so that the entire outer surface of the container body 10b is coated with the barrier material 35m, including the bottom, sidewall 10w, neck 12 and optionally the stopper 18 and/or lip 13 adjacent the stopper 18. In other embodiments, less than all but more than a major portion (e.g., >60%) of the outer surface of the container body 10b can be coated with the barrier material 35m. The barrier material 35m can be applied to the containers 10s in any suitable manner, such as, for example by immersing the barrier material whether by dipping up and down or moving the bottles along a defined path in a bath or vapor deposition environment and/or spraying the barrier material onto the containers 10s. No autoclave process is carried out on the container 10 after the barrier coating is applied and the container, after curing the barrier material 35m to adhere to the external wall of the container, is ready to ship/use and is shelf stable for a sufficient shelf-life of at least one year in normal environmental conditions (e.g., temperature, pressures and the like).

In some embodiments, as shown in FIG. 3A, the containers 10s can be suspended using a stopper holder or attachment feature 18h that can allow the body of the container 10b to be exposed without occluding coverage during the applying of the barrier material 35m to thereby allow for 360 degree coverage/exposure of the entire external surfaces of the molded container body 10b including the bottom, sidewall and neck. The holder 18h can optionally include a portion that is molded into or releasably attaches to the stopper to cooperate with a hook or other mechanical device. The holder 18h may be an external mechanical clamp that clamps against opposing sides of an external perimeter of the stopper. Other attachment configurations may be used.

In some embodiments such as in spray coating, the container holding apparatus or the coating application apparatus can be configured to rotate or turn to allow 360 degree coverage/exposure of the entire (or greater than 60%) of the external surface of the molded container body. In other embodiments, multiply spray jets 18j (FIG. 3B) stationary or translating) can be used to project/spray the material 35m outward for full or desired container coverage. Robotic application can also be used.

In some embodiments, the container can be enclosed inside an apparatus or housing and a vapor of aluminum oxide or other suitable barrier material 35m can be deposited onto the external surface (non-covered) of the container.

The gas barrier material 35m can be any suitable gas barrier material that allows the container 10 to be substantially impermeable and visually transmissive to allow for evaluation of the internal content from the sample in the container.

In some embodiments, the gas barrier material 35m can alter the oxygen transmission rate of the container 10 from about 0.120 cc/container/day/atm air without the barrier material outer coating 35c to about 0.009, about 0.008, about 0.007, about 0.006, about 0.005, about 0.004, or about 0.003 cc/container/day/atm air with such coating 35c.

In some embodiments, the barrier material 35m can be applied as a coating 35c using an aqueous solution such as Oxy-Bloc® clear finish coating from The Akzo Nobel Company, Strongsville, Ohio, USA. The coating 35c can comprise a polyetheramine such as a polyhydroxyaminoether or salt thereof.

In some embodiments, the barrier material 35m can comprise a polyepoxy-based resin and/or polyurethane polymer based on polyepoxy resin such as Phenoxy resin products from InChem, South Carolina, USA.

In some embodiments, the barrier material can comprise a polyamine or epoxy based resin such as Maxive® gas barrier resin sold by Mitsubishi Gas Chemical Company, Inc., Tokyo, Japan.

In some embodiments, the barrier material can comprise a polyvinylidene chloride (PVDC) such as Daran® from Owensboro Specialty Chemical Inc. (Owensboro, Ky., USA) or Serpene® from Dow Chemical (Buffalo Grove, Ill., USA).

In some embodiments, the barrier material can comprise a polyurethane coating such as Takelac® from Mitsui Chemical Company (Tokyo, Japan).

In some embodiments, the barrier material can comprise a nanocomposite such as SunBar® from SunChemical Inc. (Parsippany, N.J., USA), or Ormocer liquid lacquer from Fraunhofer-Institut Silicatforschung (Munchen, Germany).

In some embodiments, the barrier material can comprise a vapor deposited coating such as Freshure Technology from Knowfort Technologies BV (the Netherlands).

In some embodiments, the barrier material can comprise a polyvinyl alcohol (PVOH) or modified PVOH such as EnvironClear from Container Corporation of Canada (Toronto, Canada), or Michem®Flex from Michelman (Cincinnati, Ohio, USA), or Mica coating from Mica company.

Examples of other barrier materials that can be used in coatings include polyesters, PVDC, PVOH, PAN, PA, polyamide (PA) polyurethanes, acrylic polymers, polyetheramines, nanocomposites, and metal oxide such as aluminum oxide. Polyetheramines are reported to have high barrier and good reshaping characteristics as is seen, for example, in U.S. Pat. No. 5,472,753 to Farha, in connection with beverage bottle manufacture. It is known that the barrier properties of a polymer may be improved by the addition of impermeable plate like structures such as kaolin, vermiculite, montmorillonite and so forth. See also, U.S. Pat. Nos. 4,528,235; 4,536,425; 4,911,218; 4,960,639; 4,983,432; 5,091,467; and 5,049,609; and International Patent Application No. WO93/04118, published Mar. 4, 1993, among others. Other known nanocomposite gas barrier coatings which may be suitable are disclosed in the following: U.S. Pat. No. 7,078,453, entitled "Barrier Coating of a Non-Butyl Elastomer and a Dispersed Layered Filler in a Liquid Carrier and Coated Articles", to Feeney et al.; U.S. Pat. No. 7,119,138, entitled "Barrier Coating of a Mixture of Cured and Uncured Elastomeric Polymers and a Dispersed Layered Filler in a Liquid Carrier and Coated Articles", to Feeney et al.; and U.S. Pat. No. 7,473,729, entitled "Barrier Coating Mixtures Containing Non-Elastomeric Acrylic Polymer with Silicate Filler and Coated Articles", to Feeney et al., as well as copending United States Patent Applications Publication Nos. US 2007/0213446, entitled "Barrier Coating of a Non-Elastomeric Polymer and a Dispersed Layered Filler in a Liquid Carrier and Coated Articles", of Feeney et al.; US 2008/0131707, entitled "Concentrated Aqueous Nanocomposite Dispersions for Barrier Coatings", of Feeney et al.; and US 2006/0110615, entitled "Multilayer Nanocomposite Barrier Structures", of Karim et al., the disclosures of which are incorporated herein by reference. Other suitable gas barrier materials 35m may include, for example, a laminate film such as a polypropylene film with reprocessed/recycled polyhydroxyamino ether (PHAE) as described in US 2008/0014429 and polyetheramine nanocomposite barrier coatings as described in WO/2011/016838 and U.S. Provisional Priority Application 61/273,004. The contents of the above documents are hereby incorporated by reference as if recited in full herein.

The container body 10b can be a blow-molded body. Examples of blow-fill processes are described in U.S. Pat. Nos. 4,584,823, 4,995,519, 5,090,581, 5,356,052, 6,383,166, 6,860,405 and 7,028,862, the contents of which are hereby incorporated as if recited in full herein. However, other molding processes may be used. Although typically provided as a solid pre-formed stopper that is placed in an upper portion of the molded body, the stopper can be formed in situ in a respective mold (e.g., the top of the container body can be pinched together after filling with growth media and sensor material 14, 21, respectively, or molded to have an integral septum, not shown). If an integral septum is molded to the upper portion of the container body, it may be the same or a different material from the container body and may have increased thickness than the upstanding side wall of the container body.

The container body 10b can have a single monolithic layer of molded polymer material. In particular embodiments, the container body 10b can be formed of a thermoplastic material. The material can be, for example, one or combinations of materials including one or more of polycarbonate, polyolefin, polyester, polyethylene and nylon.

The stoppers 18, sensor material 21 and growth media 14 can be sterilized using conventional sterilization techniques, such as, for example, one or more of sterilization processes, autoclaving, gamma irradiation or ethylene oxide vapor hydrogen peroxide.

Further, the exterior surfaces of the container 10 with the barrier coating 35c can be sterilized without using autoclaving but is not required to be so processed, such as with an alcohol wipe and/or surface decontamination with VHP (vaporous hydrogen peroxide).

Figure 4:
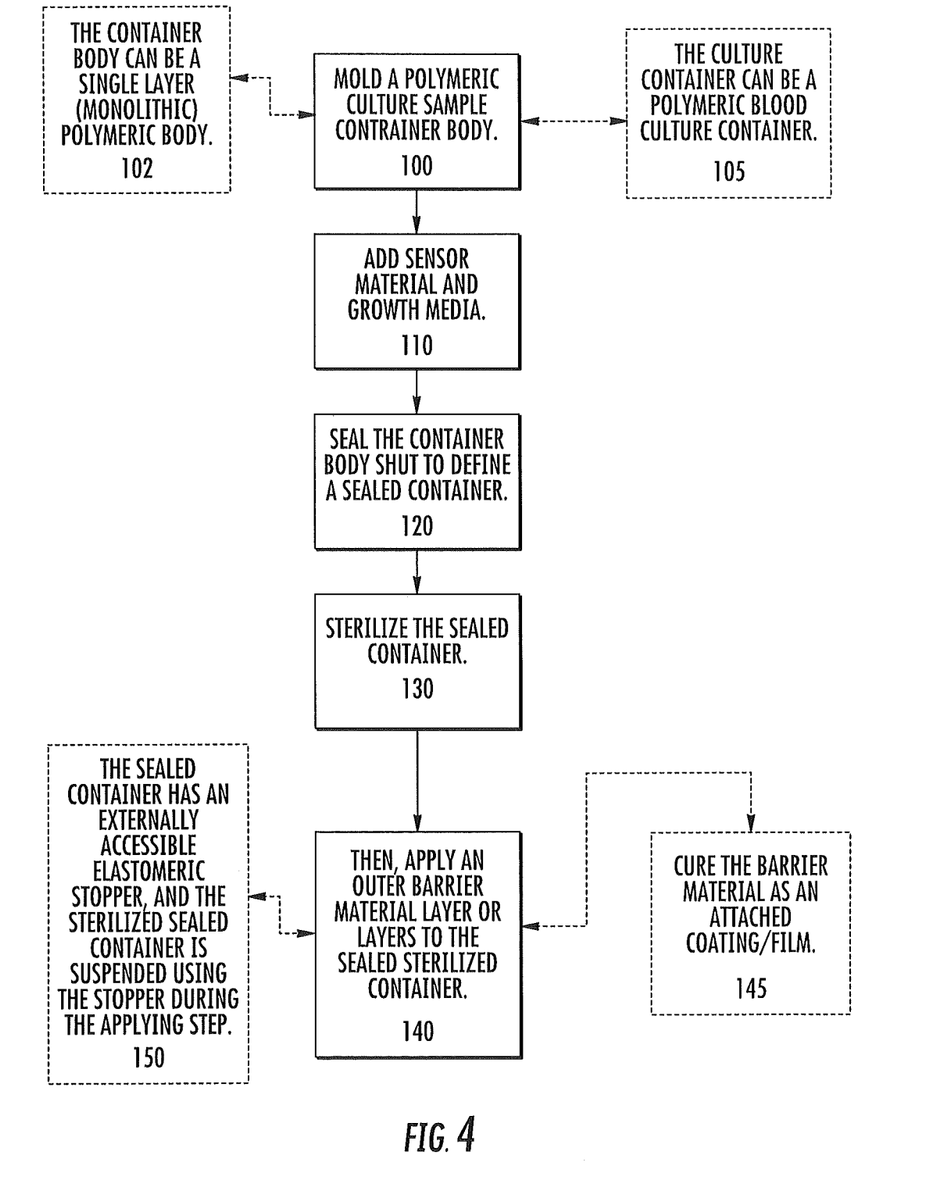
FIG. 4 is a flow chart of processing operations that can be used to carry out embodiments of the present invention.

FIG. 4 illustrates various process operations that can be used to fabricate culture sample containers according to embodiments of the present invention. A polymeric culture sample container body is molded (block 100). In a preferred embodiment, the molding can be carried out to produce a single layer (monolithic) container body (block 102). The sample container can be a blood sample culture container (block 105). Sensor material and growth media can be added (block 110). The container body can be sealed shut to define a sealed container (block 120). The sealed container is sterilized (block 130). Then, an outer barrier is applied to the sealed sterilized container (block 140). The outer barrier material on the sealed container can be cured into an attached continuous coating (block 145). The curing can be carried out at a time and elevated temperature and/or using UV or IR light.

Optionally, the sterilized sealed container can be suspended using an externally accessible elastomeric stopper on the upper portion of the container during the applying step to thereby allow for 360 degree coverage/exposure (block 150).

One of the exemplary uses of the containers 10 is in culturing a test sample to detect microbial growth in test sample (e.g., a blood sample). The method includes: (a) providing a specimen container 10 including a culture/growth medium 14 for promoting and/or enhancing growth of the microorganism; (b) introducing a test sample/specimen into the container; (c) incubating the specimen container the test sample (e.g., by placing the bottle in an incubation instrument); and (d) monitoring the specimen container for microorganism growth, either manually or automatically.

The present invention is explained in greater detail in the following non-limiting Examples.

EXAMPLES

Example 1

Sabic Lexan 124 polycarbonate was used to manufacture the monolayer plastic test sample container/vial. For preliminary study purposes as to suitability of the process, the plastic vial/container with dimensions of a current BacTALERT® bottle available from BioMerieux, Inc., Durham, N.C., USA, was coated externally by hand-dipping into a milky water-based solution—Oxy-Bloc™. Afterwards, the coated vial was placed in an 80° C. oven for about 4 minutes. After thermal cure, the external coating transformed from milky to transparent. Afterwards, the hand-dipping and thermal curing was repeated to apply a double layer of the gas barrier coating. The oxygen transmission rates of the bare plastic vial and externally coated vial are compared here in Table 1. The results show that this thin external coating significantly decreased the oxygen transmission rate to reach the current multilayer product level.

TABLE 1

OTR of Oxy-Bloc ™ Coated Bottles

| Vial Structure | Oxygen Transmission Rate (cc/bottle/day/atm air) (0% RH, 20 deg. C.) |
|---|---|
| Polycarbonate single layer | 0.120 ± 0.0023 |
| Polycarbonate single layer with Oxy-Bloc ™ | 0.006 |
| Current multilayer vial | 0.005 |

Note:
all oxygen transmission rates in this patent were tested with MOCON Oxtran 2/61 Oxygen Permeability Instrument per standard ASTM F-1307.

Example 2

Sabic Lexan 124 polycarbonate (PC) or Topas cyclic olefin copolymer (COC) were used to manufacture the plastic vials. For preliminary study purpose, the plastic vials (again the plastic vial/container had dimensions of a current BacTALERT® bottle available from BioMerieux, Inc., Durham, N.C., USA) were coated externally by hand-dipping into a coating solution. This coating solution was Maxive® coating material (35% net solid mass, two part system, mixing of M-100 with C-93) available from Mitsubishi Gas Chemical Company. Before the hand dipping application, the bottles were plasma treated for better coating adhesion. After hand-dipping the vials into the coating solution, the coated vials were placed in an 85° C. oven for about 30 min. For improved coating adhesion, several vials were treated with plasma before being coated. Also, certain bottles were pre-coated internally with silica oxide coating. The calculated coating thickness of Maxive® material is about 20 microns. The oxygen transmission rates of the bare plastic vial and externally coated vial are compared here in Table 2. The results show that this thin external coating significantly decreased the oxygen transmission rate to reach the multilayer product level.

TABLE 2

OTR of Maxive Coated Bottles

| Vial Structure | Oxygen Transmission Rate (cc/bottle/day/atm air, 20° C./0% RH) |
|---|---|
| PC single layer bottle | 0.120 ± 0.0023 |
| PC single layer bottle externally coated with Maxive ™ | 0.005 |
| PC single layer bottle externally coated with Maxive ™ and internally coated with SiOx | 0.003 |
| COC single layer bottle | 0.068 |
| COC single layer bottle externally coated with Maxive ™ | 0.006 |

TABLE 2-continued

OTR of Maxive Coated Bottles

| Vial Structure | Oxygen Transmission Rate (cc/bottle/day/atm air, 20° C./0% RH) |
|---|---|
| COC single layer bottle externally coated with Maxive ™ and internally coated with SiOx | 0.002 |
| Current multilayer bottle | 0.005 |

Example 3

Sabic Lexan 124 polycarbonate (PC) was used to manufacture the monolayer plastic vials. The plastic vials were manufactured into BacT/ALERT FN Plus products (bioMerieux, Durham, N.C.). These products were then coated externally using a laboratory curtain coater. This coating solution was Oxy-Bloc™ available from Akzo Nobel. After coating, the vials passed through a pair of infrared (IR) light lamps. For improved coating performance, certain bottles were top coated with various coating solutions after they were coated with the Oxy-Bloc™. The oxygen transmission rates of the plastic vial and externally coated vial are compared here in Table 1 To measure oxygen transmission rates of BacT/ALERT products (sterile liquid filled sealed plastic vials), the crimped cap, rubber stopper, and the media were removed before the OTR testing. The results show that this thin external coating significantly decreased the oxygen transmission rate 10× or 20× to almost reach the multilayer product level.

TABLE 3

OTR of Oxy-Bloc ™ Coated Bottles

| Bottles/Vials | ATM OTR (cc/bottle/day/atm air, 20° C., 40% RH) |
|---|---|
| PC Single layer | 0.120 |
| Flame treated, double coating of Oxy-Bloc | 0.008 |

TABLE 3-continued

OTR of Oxy-Bloc ™ Coated Bottles

| Bottles/Vials | ATM OTR (cc/bottle/day/atm air, 20° C., 40% RH) |
|---|---|
| Flame treated, double coating of Oxy-Bloc, top coated with S160 | 0.006 |
| Flame treated, double coating of Oxy-Bloc, top coated with SB | 0.007 |
| Single coating of Oxy-bloc | 0.009 |
| Single coating of Oxy-bloc, top coat of SB345 | 0.006 |
| Current multilayer bottle | 0.003 |

Example 4

Sabic Lexan 124 polycarbonate was used to manufacture the monolayer plastic test sample container/vial. These monolayer plastic vials were manufactured into BacT/ALERT SA products. These empty bottles or BacT/ALERT products were then coated externally by dipping the bottles using an automatic arm into coating solutions. Afterwards, the coating were cured in an oven per coating supplier's instructions. The oxygen transmission rates of the plastic vial and vial products are compared in Table 4. To measure oxygen transmission rates of BacT/ALERT products (sterile liquid filled sealed plastic vials), the crimped cap, rubber stopper, and the media were removed before the OTR testing. The results show that thin external coatings in this example such as Daran from Owens Specialty Chemical Company, Takelac from Mitsui Chemical Company, and Maxive® coating material from Mitsubishi Gas Chemical Company all significantly decreased the oxygen transmission rate of polycarbonate monolayer vials. The OTR of PC monolayer bottles coated with about 20 micron Maxive® for this sample is 0.008 cc/bottle/day/atm (measured at 20 C and 40%RH), slightly different than the 0.005 cc/bottle/day/atm (measured at 20 C at 0%RH) for the similar sample in Example 2. These two samples were coated by two different coaters and bottles in Example 2 were plasma treated while the bottles in this example were not plasma treated.

TABLE 4

OTR of Bottles Coated With Various Coatings

| Vial | Layer of Coating | Coat Weight (g) | Curing Condition | OTR (cc/bottle/day/atm, 20 C./40% RH) |
|---|---|---|---|---|
| PC vial | NA | NA | NA | 0.120 ± 0.0023 |
| PC/Takelac WPB341 Vial | Two | 0.30 | 110 C. 2 min | 0.027 |
| PC/Takelac WPB341 BacT | One | 0.23 | 110 C. 2 min | 0.050 |
| PC/Takelac WP BacT | Two | 0.30 | 110 C. 2 min | 0.030 |
| PC/Daran SL112 Vial | One | 0.27 | 60 C. 10 min | 0.034 |
| PC/Daran SL112 Vial | One | 0.30 | 100 C. 6 min | 0.022 |
| PC/Daran SL112 BacT | One | 0.36 | 60 C. 10 min | 0.013 |
| PC/Daran SL112 BacT | One | 0.30 | 100 C. 6 min | 0.014 |
| PC/Daran SL112 BacT | Two | 0.61 | 60 C. 10 min | 0.006 |
| PC/Daran SL112 BacT | Two | 0.63 | 100 C. 6 min | 0.010 |
| PC/Maxive Vial | One | 0.16 | 120 C. for 10 min | 0.014 |
| PC/Maxive BacT | Two | 0.25 | 120 C. for 10 min | 0.008 |
| Current multilayer BacT | NA | NA | NA | 0.004 |

Note:
1. "BacT" means the monolayer vial was manufactured into BacT/ALERT products before the OTR were tested while "Vial" means the OTR were tested on the plastic vial as received without going through the manufacturing process,
2. Coat weight of 0.25 gram roughly corresponds to 20 micron of coating thickness assuming uniform coating thickness, calculated coating area of about 125 $cm^2$ based on the bottle geometry, and density of the coating film to be 1 $g/cm^3$.

Example 5

Sabic Lexan 124 polycarbonate was used to manufacture the monolayer plastic test sample container/vial. These monolayer plastic vials were manufactured into BacT/ALERT SN products. The empty bottles or BacT/ALERT products were then sent out to companies to be coated externally with various coating solutions. The oxygen transmission rates of the plastic vial and vial products are compared in Table 5. To measure oxygen transmission rates of BacT/ALERT products (sterile liquid filled sealed plastic vials), the crimped cap, rubber stopper, and the media were removed before the OTR testing. The results show that thin external coatings in this example such as EnvironClear from Canada Container Corporation, SmartCoat from Sipa, PKHW from InChem Corporation crosslinked with melamine, polyurethanes coatings from two part system such as PKHW products and isocyanate, and a coating provided by Allied Photo Chemical Company which was cured by ultraviolet lamp all significantly decreased the oxygen transmission rate of polycarbonate monolayer vials.

TABLE 4

OTR of Bottles Coated With Various Coatings

| Vial | Layers of Coating | OTR (cc/bottle/day/atm, 20 C./40% RH) |
|---|---|---|
| PC vial | NA | 0.120 ± 0.0023 |
| PC/EnvironClearA Vial | One | 0.005 |
| PC/EnvironClearB Vial | One | 0.005 |
| PC/SmartCoatA Vial | One | |
| PC/SmartCoatB Vial | One | |
| PC/SmartCoatB BacT | One | |
| PC/PKHW-Melamine Vial | One | 0.093 |
| PC/PKHW-Melamine Vila | Two | 0.060 |
| PC/PolyurethanPKHW Vial | One | |
| PC/UVCuredCoating | One | 0.096 |
| PC/UVCuredCoating | Two | 0.08 |
| Current multilayer BacT | NA | 0.004 |

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A process for producing culture sample containers, comprising:
   introducing a colorimetric sensor material into a molded container body of a single monolithic layer of polymeric material, the container body having a container shape with a bottom and an upwardly extending wall;
   introducing growth media into the container body;
   introducing a gas or gas mixture into the container body under vacuum to define a headspace gas in an upper portion of the container body;
   attaching a stopper to the container body with the sensor material;
   sealing the container body with the stopper with the growth media and the headspace gas enclosed therein to form a sealed culture sample container; then
   sterilizing the sealed container; then
   applying a fluid gas barrier material to an exterior of the sterilized sealed container body to form a gas barrier coating as an exterior surface of the sealed culture container so that the sealed container has an oxygen transmission rate (cubic centimeter/container/day/atm air) that is between 0.00001 and 0.1; and
   providing the sealed container with the applied gas barrier coating as the exterior surface as a ready to use sealed culture sample container that is shelf stable and does not undergo post-gas barrier coating autoclaving.

2. The process of claim 1, wherein the applying the gas barrier coating step is carried out to cover substantially all external surfaces of the container body.

3. The process of claim 1, further comprising applying a top coat on the gas barrier coating, wherein the oxygen transmission rate is between 0.001 and 0.01 (cubic centimeter/container/day/atm air).

4. The process of claim 3, further comprising, after the applying step, curing the coating solution on the container body to form a thin transparent coating film that adheres to and is not detachable from the outer surface of the container body.

5. The process of claim 1, wherein the applying step is carried out to apply a first barrier coating layer, curing the first barrier coating layer, then applying a second barrier coating layer or a top coat.

6. The process of claim 1, wherein applying the gas barrier coating is carried out either (a) using a gas barrier material that, after curing, defines a transparent film that adheres to the outer surface of the container body or (b) vapor-depositing a thin layer onto the container body.

7. The process of claim 1, wherein the polymeric material comprises polycarbonate (PC) or cyclic olefin copolymer (COC).

8. The process of claim 1, further comprising curing the gas barrier coating into a monolayer transparent film or a vapor deposited transparent layer having a thickness between about 1 micron to 1000 microns.

9. The process of claim 1, further comprising, before the introducing, attaching and applying steps, coating an internal surface of the container body with silica oxide.

10. The process of claim 1, further comprising, before the sterilizing step and after attaching the stopper, crimping a cap onto the sealed container, wherein the applied gas barrier coating is a mono-layer transparent film or vapor-deposited transparent layer that has a thickness that is between about 10-100 microns, on average, wherein the sealed container body has a shelf life of one year or more and can maintain 90% of its draw volume, and wherein the oxygen transmission rate is between 0.001 and 0.01 (cubic centimeter/container/day/atm air).

11. The process of claim 1, further comprising applying an internal coating onto interior surfaces of the container body before the introducing steps.

12. The process of claim 1, wherein the container body bottom is substantially flat.

13. The process of claim 1, further comprising, before the sterilizing step and after attaching the stopper, crimping a cap onto the sealed container, wherein the colorimetric sensor material comprises Liquid Emulsion Silicone (LES), wherein the applied gas barrier coating is a mono-layer transparent film or a vapor-deposited transparent layer that has a thickness that is between about 10-30 microns, on average, wherein the sealed container body has a shelf life of one year or more, and wherein the oxygen transmission rate is between 0.001 and 0.01 (cubic centimeter/container/day/atm air).

14. The process of claim 1, further comprising suspending the sterilized sealed container during the applying step to thereby expose the container body to allow the gas barrier coating material to coat the entire container body.

15. The process of claim 1, wherein the culture container is a blood sample container for culturing microbes in a blood sample.

16. The process of claim 1, wherein the step of applying the gas barrier coating is carried out so that the sealed culture container has a monolayer barrier coating that is between 1 and 1000 microns thick and the sealed, sterilized container with the post-seal and post-sterilization gas barrier coating oxygen transmission rate that is between about 0.001 to about 0.01 (cubic centimeter/container/day/atm air).

17. The process of claim 1, wherein the step of applying the gas barrier coating is carried out to define a sealed container with a bi-layer external gas barrier coating that has an oxygen transmission rate that is between about 0.001 to about 0.009 (cubic centimeter/container/day/atm air).

18. The process of claim 1, wherein the container body has an upper portion with a shoulder and neck, and wherein the container body is visually transmissive with a wall having a wall thickness that is between about 0.5 and 5 mm.

19. A process for producing monolayer polymeric culture sample containers, comprising:
   introducing a colorimetric sensor material comprising Liquid Emulsion Silicone (LES), into a molded container body of a single monolithic layer of polymeric material, the container body having a container shape with a bottom and an upwardly extending wall, wherein the upwardly extending has a wall thickness that is between about 0.5 and 5 mm;
   introducing growth media into the container body;
   introducing a gas or gas mixture into the container body under vacuum to define a headspace gas in an upper portion of the container body;
   sealing the container body with a stopper enclosing the growth media and the headspace gas therein; then
   autoclaving the sealed container body with the growth media and headspace gas enclosed therein; then
   applying then curing a fluid gas barrier coating to an exterior of the sterilized sealed container body while the sealed container body encloses the growth media and headspace gas therein to define a sealed culture container with the gas barrier coating as an exterior surface that is ready-to-use and shelf stable without post-gas barrier coating autoclaving, wherein the sealed culture container has a shelf life of one year or more and, measured at one year, can maintain 90% of its draw and has an oxygen transmission rate (cubic centimeter/container/day/atm air) that is between 0.001 and 0.01, and wherein the sealed container body with the applied gas barrier coating is visually transmissive.

20. The process of claim 19, wherein the applied gas barrier coating is a mono-layer transparent film or a vapor-deposited transparent layer that has a thickness that is between about 10-30 microns, on average.

* * * * *